(12) United States Patent
Kuzmin et al.

(10) Patent No.: US 9,458,068 B2
(45) Date of Patent: Oct. 4, 2016

(54) PROCESS AND VESSEL FOR REMOVING ONE OR MORE SULFUR COMPOUNDS

(71) Applicants: UOP LLC, Des Plaines, IL (US); Boreskov Institute of Catalysis, Siberian Branch of Russian Academy of Sciences, Novosibirsk (RU)

(72) Inventors: Andrey Kuzmin, Novosibirsk (RU); Aziz Sattar, West Chicago, IL (US); Lev Davydov, Northbrook, IL (US); Jonathan Andrew Tertel, Mt. Prospect, IL (US)

(73) Assignees: UOP LLC, Des Plaines, IL (US); BORESKOV INSTITUTE OF CATALYSIS, Novosibirsk (RU)

( * ) Notice: Subject to any disclaimer, the term of this patent is extended or adjusted under 35 U.S.C. 154(b) by 725 days.

(21) Appl. No.: 13/709,613

(22) Filed: Dec. 10, 2012

(65) Prior Publication Data

US 2014/0163298 A1    Jun. 12, 2014

(51) Int. Cl.
   *C07C 7/10*       (2006.01)
   *B01D 11/04*      (2006.01)

(52) U.S. Cl.
   CPC .................. *C07C 7/10* (2013.01); *B01D 11/04* (2013.01); *B01D 11/0461* (2013.01)

(58) Field of Classification Search
   CPC ...... C07C 7/10; B01D 11/04; B01D 11/0461
   See application file for complete search history.

(56) References Cited

U.S. PATENT DOCUMENTS

| | | | |
|---|---|---|---|
| 2,659,664 A | 11/1953 | Works et al. | |
| 3,784,009 A | 1/1974 | Maciula | |
| 3,867,103 A | 2/1975 | Boney et al. | |
| 4,604,988 A | 8/1986 | Rao | |
| 5,098,668 A | 3/1992 | Callen et al. | |
| 5,405,497 A | 4/1995 | Torregrossa | |
| 5,462,639 A | 10/1995 | Matthews et al. | |

(Continued)

FOREIGN PATENT DOCUMENTS

| | | |
|---|---|---|
| EP | 1406731 | 5/2005 |
| KR | 972921 | 7/2010 |

OTHER PUBLICATIONS

AM Ende et al., "Interfacial Area of Dispersions of Sulfuric Acid and Hydrocarbons", Industrial & Engineering Chemistry Research, Dec. 1995, vol. 34, No. 12, pp. 4343-4350.

(Continued)

*Primary Examiner* — David A Reifsnyder

(57) ABSTRACT

One exemplary embodiment can be a process for removing one or more sulfur compounds from a first liquid. The process can include passing the first liquid through a first inlet and a second liquid through a second inlet of a vessel, passing the first and second liquids through the passageway for facilitating contacting of the first and second liquids to extract the one or more sulfur compounds from the first liquid to the second liquid, and passing the first liquid through the first outlet and the second liquid through the second outlet. Often, the vessel has a plurality of vortex contactors, and a first outlet and a second outlet. The plurality of vortex contactors can include a first vortex contactor, in turn having at least one wall forming a perimeter about an interior region and including a first side and a second side forming a passageway communicating the first liquid from an exterior to the interior region, and a frustum positioned proximate to the passageway and abutting the at least one wall.

11 Claims, 11 Drawing Sheets

(56) References Cited

U.S. PATENT DOCUMENTS

| | | |
|---|---|---|
| 6,241,809 B1 | 6/2001 | Hopkins |
| 6,303,843 B1 | 10/2001 | Anderson et al. |
| 6,322,763 B1 | 11/2001 | McDaniel |
| 6,430,937 B2 | 8/2002 | Cho et al. |
| 6,464,210 B1 | 10/2002 | Teran et al. |
| 6,576,029 B2 | 6/2003 | West |
| 6,709,500 B1 | 3/2004 | West |
| 6,852,902 B2 | 2/2005 | Smith, Jr. |
| 7,126,038 B2 | 10/2006 | Smith, Jr. |
| 7,326,333 B2 | 2/2008 | Laricchia et al. |
| 8,028,975 B2 | 10/2011 | Tertel et al. |
| 2009/0115076 A1 | 5/2009 | Makhotkin et al. |
| 2009/0221863 A1 | 9/2009 | Strauss et al. |
| 2009/0283474 A1 | 11/2009 | Achard et al. |
| 2010/0258427 A1 | 10/2010 | Towler |
| 2011/0239862 A1 | 10/2011 | Davydov |
| 2012/0000827 A1 | 1/2012 | Krupa et al. |
| 2014/0163294 A1* | 6/2014 | Sattar ................ B01D 11/0446 585/802 |

OTHER PUBLICATIONS

Baird et al., "Liquid-Liquid Extraction Using Vortex Rings in a Batch Cell", Trans IChemE, Jul. 1992, vol. 70, No. A4, pp. 323-332.
Abstract of CN 1490070 Publication Date Apr. 21, 2004 by Zhang Wenfei.
Abstract of CN 201258914 Publication Date Jun. 17, 2009 by Luoyang Siyite Bearing Co. Ltd.
Abstract of CN 2573055 Publication Date Sep. 17, 2003 by Zhang Wenfei.
Martin et al., "Tangential Flow Development for Laminar Axial Flow in an Annulus With a Rotating Inner Cylinder", Proc. R. Soc. Lond. A., May 2, 1972, vol. 328, No. 1572, pp. 123-141.
"Vortex De-Pollution System—The Leading Solution That Meets UK Legislation Requirements", at www.vortexdepollution.com/lpg.html, 2008, p. 6 screen pages.
"LPG Recovery from End of Life Vehicles", at www.atfprofessional.co.uk/lpgrecovery.aspx, p. 1 screen page, Dec. 19, 2011.
Weinstein et al., "Liquid-Liquid Contacting in Unbaffled, Agitated Vessels", AIChE Seventy-Fourth National Meeting New Orleans, LA, Mar. 11, 1973, Volume Paper, No. 91A, p. 40 Pages.

* cited by examiner

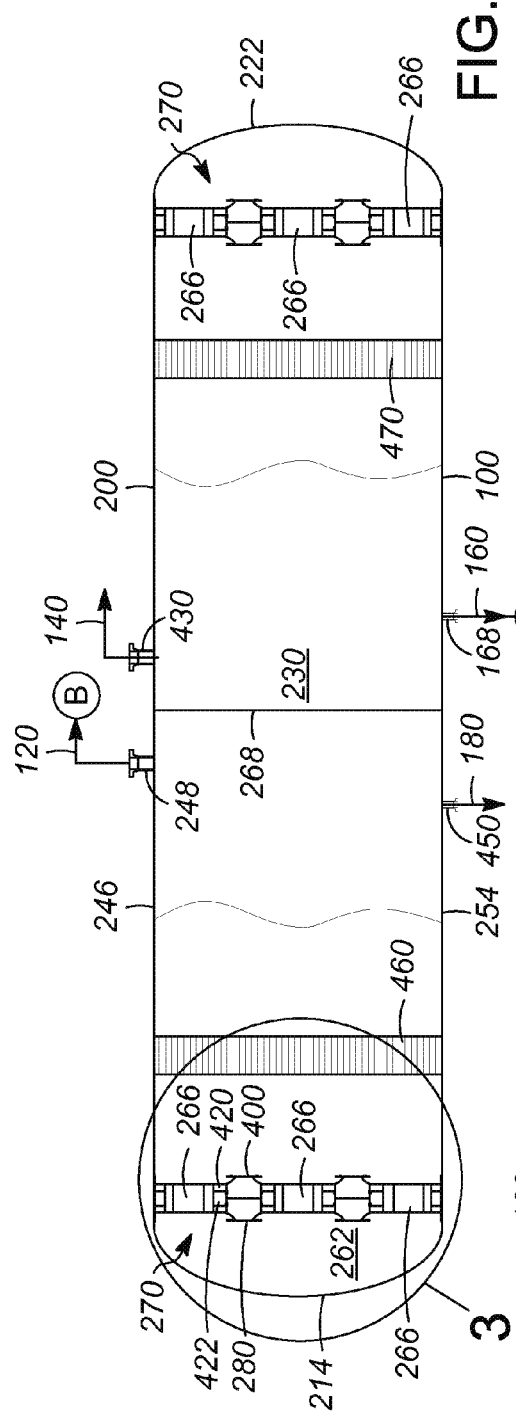

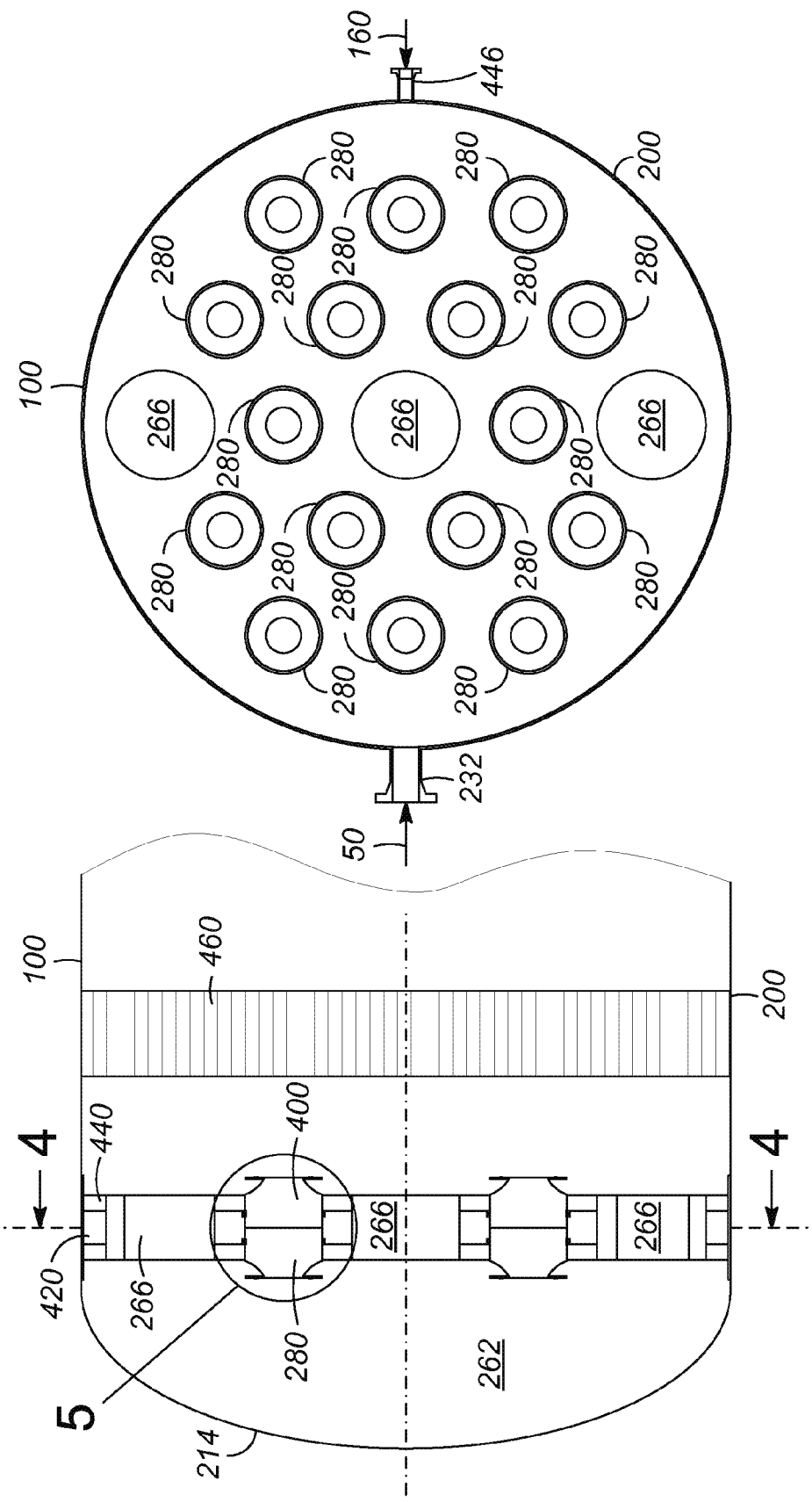

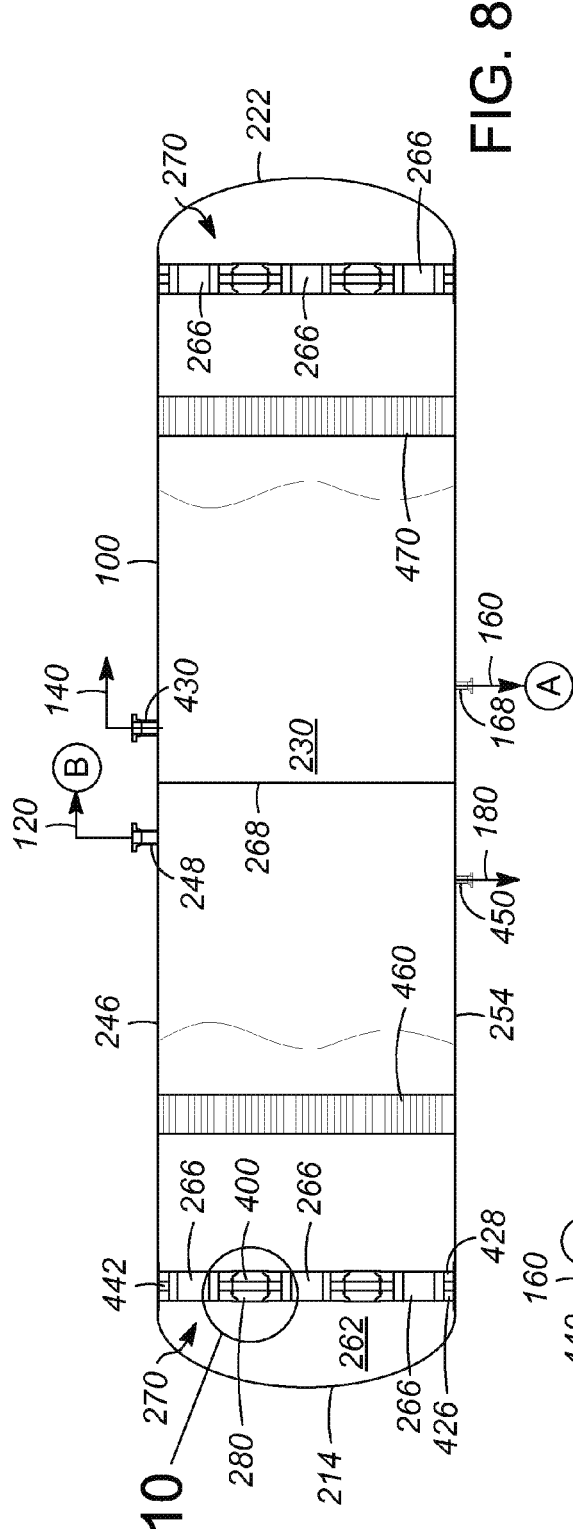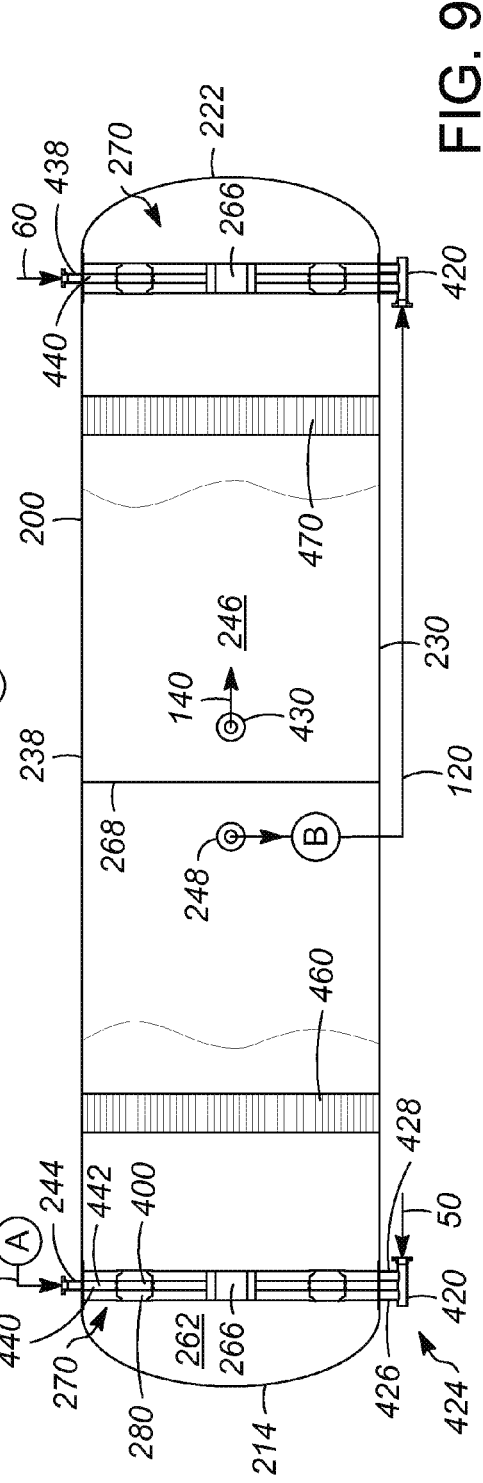

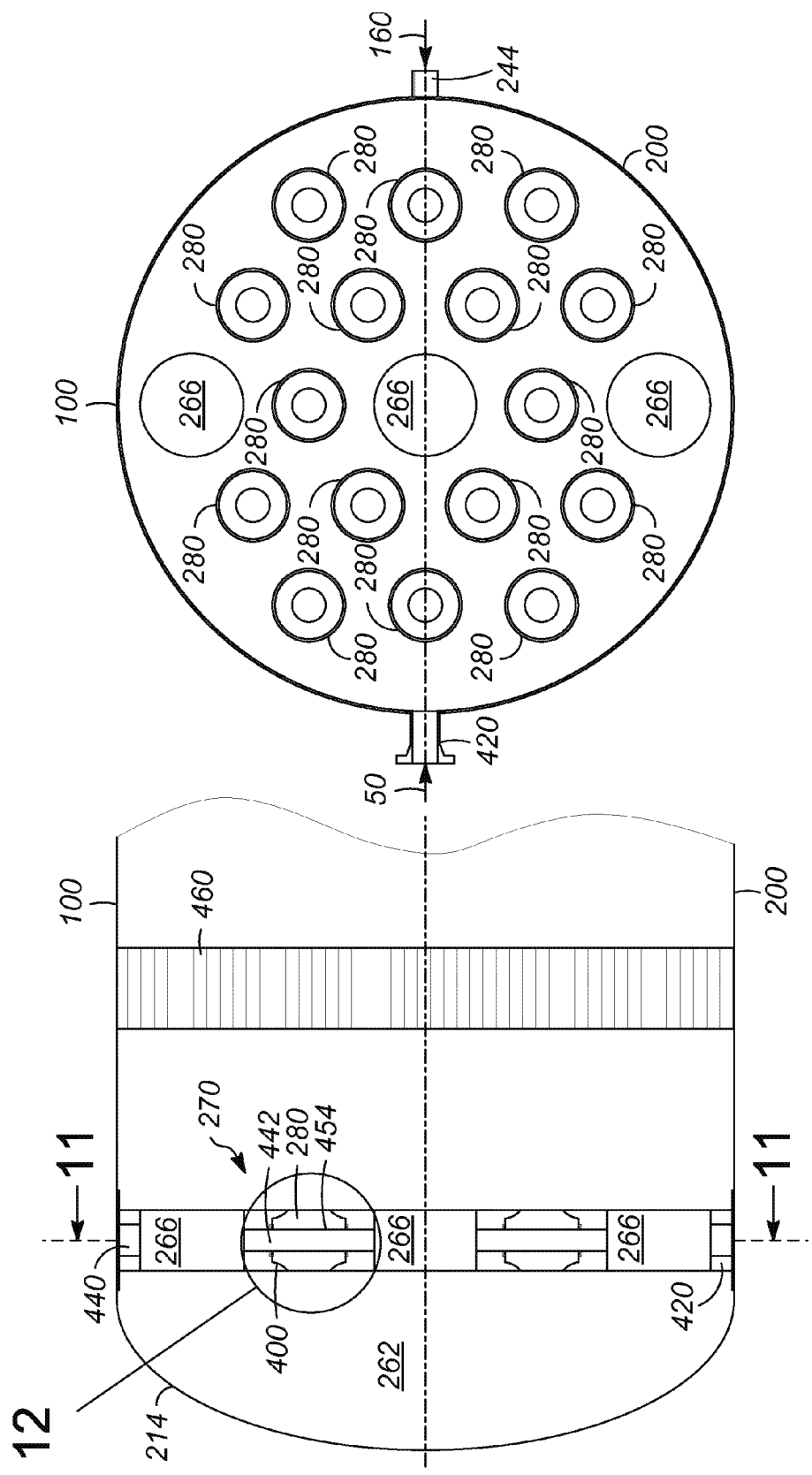

PROCESS AND VESSEL FOR REMOVING ONE OR MORE SULFUR COMPOUNDS

FIELD OF THE INVENTION

This invention generally relates to a process and a vessel for removing one or more sulfur compounds.

DESCRIPTION OF THE RELATED ART

Current industry practice to extract one or more mercaptan compounds from a hydrocarbon stream can use a water-based caustic solvent. Often, the hydrocarbon stream and the caustic solvent are mixed and then the hydrocarbon and aqueous phases are separated by settling or decanting. The mixing and phase separation operations may be done in a stage wise manner typically involving mechanically or hydraulically-driven intimate mixing of the two phases followed by a settling stage. Generally, the settling stage requires a large vessel volume, such as a large diameter and a tangent length, to allow the dispersed phase to coalesce and separate from the continuous phase under near stagnant conditions. Usually, this large volume minimizes the entrainment or carryover of the dispersed phase in the continuous phase as it exits the settling volume.

Alternatively, a vertically oriented column with multiple stages of contacting trays for liquid-liquid extraction of primarily mercaptan sulfur contaminants from one or more hydrocarbons may use caustic as a solvent in a countercurrent flow configuration. Typically, the last tray before the treated hydrocarbon exits the column is followed by a disengaging distance for gravity-aided coalescing/settling of caustic, often followed by a wire mesh packing or other coalescing media that can provide the fine coalescing/separating of two immiscible liquids. The packing, in turn, is usually followed by an overhead disengaging volume to allow for further separation of caustic from hydrocarbons. Yet another approach for separating caustic from hydrocarbon may utilize a non-dispersive contacting device, such as a fiber film contactor, for extraction followed by a horizontal settler that allows for further separation of caustic from hydrocarbon primarily from droplet coalescence and gravity settling.

The alternate approach already in practice based on use of a mixer-settler device can be amenable to modular supply because the contacting device usually does not require extra ordinary field erection equipment. However, such mixer-settler devices may fail to achieve the required phase mixing and phase separation. Thus, it is desirable to obtain a device that provides the required phase mixing and separation while minimizing the number and size of vessels to facilitate transportation and installation.

SUMMARY OF THE INVENTION

One exemplary embodiment can be a process for removing one or more sulfur compounds from a first liquid. The process can include passing the first liquid through a first inlet and a second liquid through a second inlet of a vessel, passing the first and second liquids through the passageway for facilitating contacting of the first and second liquids to extract the one or more sulfur compounds from the first liquid to the second liquid, and passing the first liquid through the first outlet and the second liquid through the second outlet. Often, the vessel has a plurality of vortex contactors, and a first outlet and a second outlet. The plurality of vortex contactors can include a first vortex contactor, in turn having at least one wall forming a perimeter about an interior region and including a first side and a second side forming a passageway communicating the first liquid from an exterior to the interior region, and a frustum positioned proximate to the passageway and abutting the at least one wall.

Another exemplary embodiment can be a vessel for removing one or more sulfur compounds. The vessel can include a substantially cylindrical shell orientated substantially horizontal, a plurality of vortex contactors arranged radially in the interior space, and a first manifold communicating a first liquid and a second manifold communicating a second liquid to each of the plurality of vortex contactors and their respective passageways. Generally, the shell has a first end, a second end, a first side, a second side, a top, and a bottom and surrounds an interior space. Often, the plurality of vortex contactors has a first vortex contactor and a second vortex contactor with the first vortex contactor abutting the second vortex contactor. Additionally, the first vortex contactor can include at least one wall forming a perimeter about an interior region and having a first side and a second side forming a passageway communicating a first liquid and a second liquid from an exterior to the interior region, and a frustum positioned proximate to the passageway and abutting the at least one wall.

A further exemplary embodiment may be a vessel for removing one or more sulfur compounds. The vessel can include a substantially cylindrical shell orientated substantially vertical, an internal compartment positioned within the substantially cylindrical shell, and a plurality of vortex contactors arranged radially in the interior space. Generally, the shell includes a first end, a second end, a first side, a second side, a top, and a bottom and surrounds an interior space. Usually, the plurality of vortex contactors has a first group of vortex contactors at a first elevation and a second group of vortex contactors at a second elevation inside the internal compartment. A first vortex contactor of the plurality of vortex contactors can include at least one wall forming a perimeter about an interior region and having a first side and a second side forming a passageway communicating a first liquid and a second liquid from an exterior to the interior region, and a frustum positioned proximate to the passageway and abutting the at least one wall.

The embodiments disclosed herein are amenable to modular supply by use of contacting and extraction separation devices. The embodiments may utilize either a horizontally or vertically oriented vessel to house internal components designed to extract one or more sulfur compounds from one or more hydrocarbons by contact with an alkaline liquid, typically an aqueous solvent such as a dilute sodium hydroxide solution. The embodiments employed herein can utilize a contacting and extraction device, such as a vortex extractor. Multiple vortex contactors can be mounted for parallel operation on a structure resembling a tray contained within a vessel. Generally, the vortex contactors are highly efficient and require fewer contacting stages to achieve the same extraction capability as various embodiments of contacting trays.

In one exemplary embodiment, the trays can contain multiple vortex contactors housed in a horizontal vessel. The horizontal orientation can facilitate modular equipment supply by minimizing the equipment erected in the field. In another embodiment, the trays can contain multiple vortex contacting devices housed in a lower profile vertical vessel. The reduced number of contacting trays can allow the vessel length to be reduced by approximately 50% as compared to other contacting tray designs. The embodiments employed herein can also utilize coalescing media downstream of the vortex contacting devices to provide for finer separation of caustic from hydrocarbon. Moreover, the devices herein can be operated at lower g-forces, such as less than about 10 g.

DEFINITIONS

As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., C3$^+$ or C3$^-$, which is inclusive of the abbreviated one or more hydrocarbons. As an example, the abbreviation "C3$^+$" means one or more hydrocarbon molecules of three carbon atoms and/or more. In addition, the term "stream" may be applicable to other fluids, such as aqueous and non-aqueous solutions of alkaline or basic compounds, such as sodium or potassium hydroxide.

As used herein, the terms "hydrocarbon feed" and "hydrocarbon stream", and "alkaline stream" may also be referred to as, respectively, a "hydrocarbon liquid" and an "alkaline liquid".

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of generally at least about 50%, and preferably about 70%, by mole, of a compound or class of compounds in a stream. If referring to a solute in solution, e.g., one or more thiol compounds in an alkaline solution, the term "rich" may be referenced to the equilibrium concentration of the solute. As an example, about 5%, by mole, of a solute in a solvent may be considered rich if the concentration of solute at equilibrium is 10%, by mole.

As used herein, the term "substantially" can mean an amount of generally at least about 80%, preferably about 90%, and optimally about 99%, by mole, of a compound or class of compounds in a stream. If referring to a solute in solution, e.g., one or more thiol compounds in an alkaline solution, the term "substantially" may be referenced to the equilibrium concentration of the solute. As an example, about 8%, by mole, of a solute in a solvent may be considered substantial if the concentration of solute at equilibrium is 10%, by mole.

As used herein, the term "frustum" can mean a solid figure formed when a plane, which is substantially parallel to a base or a top of a cone, a pyramid, and a funnel, sections the shape. With respect to the term "funnical frustum", the sectioning plane can pass through a conical portion of the funnel and be substantially parallel to another plane perpendicular to the mouth of the funnel.

As used herein, the term "coupled" can mean two items, directly or indirectly, joined, fastened, associated, connected, or formed integrally together either by chemical or mechanical means, by processes including stamping, molding, or welding. What is more, two items can be coupled by the use of a third component such as a mechanical fastener, e.g., a screw, a nail, a staple, or a rivet; an adhesive; or a solder.

As used herein, the term "mercaptan" means thiol and can include compounds of the formula RSH as well as salts thereof, such as mercaptides of the formula RS-M$^+$ where R is a hydrocarbon group, such as an alkyl or aryl group, that is saturated or unsaturated and optionally substituted, and M is a metal, such as sodium or potassium.

As used herein, the term "disulfides" can include dimethyldisulfide, diethyldisulfide, and ethylmethyldisulfide, and possibly other species having the molecular formula RSSR' where R and R' are each, independently, a hydrocarbon group, such as an alkyl or aryl group, that is saturated or unsaturated and optionally substituted. Typically, a disulfide is generated from the oxidation of a mercaptan-tainted caustic and forms a separate hydrocarbon phase that is not soluble in the aqueous caustic phase. Generally, the term "disulfides" as used herein excludes carbon disulfide ($CS_2$).

As used herein, the weight percent or ppm of sulfur, e.g., "wppm-sulfur" is the amount of sulfur in a hydrocarbon stream, and not the amount of the sulfur-containing species unless otherwise indicated. As an example, methylmercaptan, $CH_3SH$, has a molecular weight of 48.1 with 32.06 represented by the sulfur atom, so the molecule is about 66.6%, by weight, sulfur. As a result, the actual sulfur compound concentration can be higher than the wppm-sulfur from the compound. An exception is that the disulfide content in caustic can be reported as the wppm of the disulfide compound.

As used herein, the term "g-force" can be abbreviated "g" and mean the angular acceleration imparted to a liquid and can be in units of meter per second squared (abbreviated $m/s^2$). One "g" can equal 9.8 $m/s^2$.

As used herein, the terms "intermediate" or "spent" can mean that at least some of the capacity of a second liquid for extracting compounds, such as sulfur compounds, can be at least partially impeded by at least partial saturation by the compounds, or can mean a first liquid being at least partially extracted of the compounds.

As used herein, the term "parts per million" may be abbreviated herein as "ppm" and be based on weight.

As used herein, the term "kilopascal" may be abbreviated "KPa" and all pressures disclosed herein are absolute.

As used herein, the term "immiscible" can describe substances of the same phase or state of matter that cannot be uniformly mixed or blended. As an example, such immiscible mixtures can include liquids such as oil and water, or caustic or an alkaline solution, such as a water solution of sodium hydroxide, and hydrocarbon.

As used herein, the term "abut" can mean two vortex contactors in a back-to-back orientation sharing a common wall, including a wall of conduit even if the contactors are on opposing sides of the conduit.

As used herein, the term "cross-sectional" may refer to a view of only a slice or portion of a component or apparatus without depicting underlying elements.

As depicted, process flow lines in the figures can be referred to interchangeably as, e.g., lines, pipes, liquids, feeds, products, or streams.

BRIEF DESCRIPTION OF THE DRAWINGS

FIG. 1 is a side, elevational, and partial cutaway view of an exemplary vessel.
FIG. 2 is a top, plan, and partial cutaway view of the exemplary vessel of FIG. 1.

FIG. 3 is a side, elevational, and enlarged view of the exemplary vessel of FIG. 1.

FIG. 4 is a cross-sectional view of the exemplary vessel of FIG. 3.

FIG. 8 is a side, elevational, and partial cutaway view of another exemplary vessel.

FIG. 9 is a top, plan, and partial cutaway view of the another exemplary vessel.

FIG. 10 is a side, elevational, and enlarged view of the another exemplary vessel of FIG. 8.

FIG. 11 is a cross-sectional view of the another exemplary vessel of FIG. 10.

DETAILED DESCRIPTION

Figure 5:
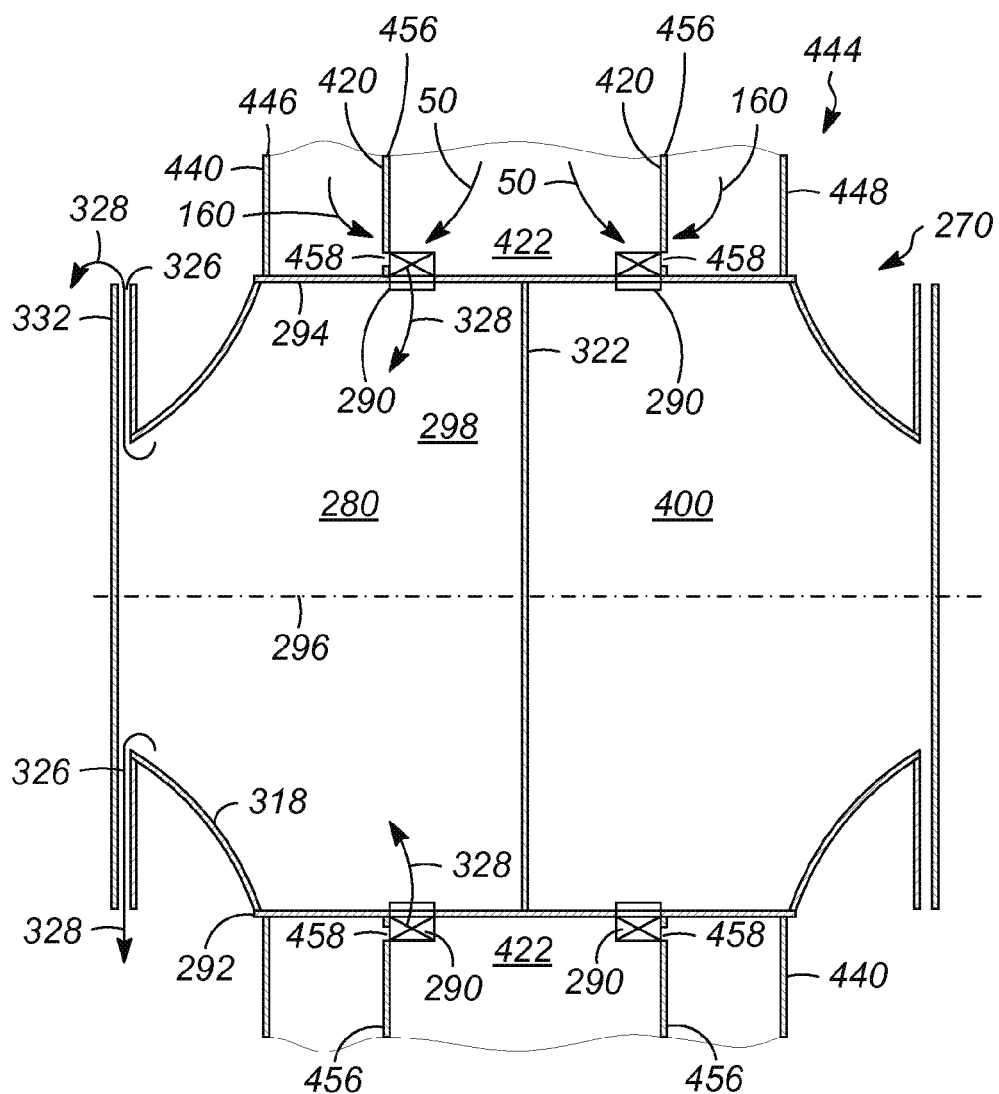
FIG. 5 is a side, elevational, and enlarged view of a portion of the exemplary vessel depicted in FIG. 3.

Referring to FIGS. 1-5, an exemplary vessel 100 for removing or extracting one or more sulfur compounds can include a first end 214, a second end 222, a first side 230, a second side 238, a top 246, and a bottom 254. Generally, the vessel 100 can include a substantially cylindrical shell 200 that is orientated substantially horizontal with the horizontal length greater than the vertical height. Often, the vessel 100 can include a first inlet 232 on the first side 230, second inlets 242 on the second side 238, a first outlet 430 on the top 246, a second outlet 450 on the bottom 254, an intermediate first liquid outlet 248 on the top 246, and an intermediate second liquid outlet 168 on the bottom 254. The vessel 100 and other associated equipment can be made from any suitable material, such as carbon steel. Desirably, the contacting of the hydrocarbon liquid and alkaline liquid is counter-current, although in other embodiments the contacting may be co-current. The first inlet 232 can be adapted to receive a first liquid 50, the second inlets 242 can be adapted to receive a second liquid 60, the first outlet 430 can provide a first liquid product 140, typically a hydrocarbon stream, and the second outlet 450 can provide a spent second liquid 180. As used in the drawings, the points "A" and "B" are merely used to aid indicating the flow paths of the intermediate first and second liquids 120 and 160 through the vessel 100, as hereinafter described.

The vessel 100 as disclosed herein can facilitate mass transfer of solute between two immiscible liquids. Although densities may be similar, one liquid is typically heavier than the other. Usually, the first liquid 50 can be lighter and less dense and the second liquid may be heavier and denser. Often, the first liquid 50 can be at least one hydrocarbon, such as a liquefied petroleum gas having one or more C1-C5 hydrocarbons or a naphtha having one or more C5-C12 hydrocarbons, and the second liquid 60 can be an alkaline solution thereof, such as a sodium hydroxide, a potassium hydroxide, or an ammonia aqueous solution. Generally, the first liquid 50 contains a substance to be extracted and/or reacted, such as one or more sulfur compounds, such as one or more thiol compounds. Often, the substance is extracted from the hydrocarbon liquid into an alkaline solution. Examples can include contacting a liquefied petroleum gas containing one or more sulfur compounds and a solution of sodium hydroxide. Such exemplary extraction processes are disclosed in, e.g., U.S. Pat. No. 7,326,333 and U.S. Pat. No. 8,028,975.

Typically, the first liquid 50 includes up to about 10,000 ppm, preferably no more than about 1,000 ppm, by weight, sulfur in one or more thiol compounds based on the weight of the first liquid 50. Often, the first liquid 50 contains sulfur compounds in the form of one or more thiol compounds and/or hydrogen sulfide as well as carbonyl sulfide, one or more sulfides, and carbon disulfide. Although not wanting to be bound by theory, usually the hydrogen sulfide and the one or more thiol compounds are extracted or removable from the hydrocarbon feed 50 in the vessel 100. The first liquid 50 may be provided at a first stage at the first end 214.

The second liquid 60 can be an aqueous alkaline solution, such as an aqueous solution of caustic soda, e.g., sodium or potassium hydroxide, or ammonia. The aqueous alkaline solution can include about 1-about 30%, by weight, of the alkaline material. Such aqueous alkaline solutions are disclosed in, e.g., U.S. Pat. No. 7,326,333. In counter-current processing, the second liquid 60 can be provided to the second stage, namely the second end 222 of the vessel 100. Partially extracted and partially saturated or spent streams, namely an intermediate first liquid 120 and an intermediate second liquid 160, may be provided to, respectively, the second end 222 and the first end 214.

The substantially cylindrical shell 200 can contain an interior space 262 that houses various components. Particularly, a plurality of vortex contactors 270 can be arranged radially at the first end 214 and the second end 222. Such vortex contactors are disclosed in, e.g., U.S. application Ser. Nos. 13/709,329 and 13/709,376, both by Kuzmin et al., filed herewith, which are hereby incorporated by reference in their entirety. In this exemplary embodiment, the plurality of vortex contactors 270 can include contactors 280 and 400 arranged back-to-back with sixteen vortex contactors 280 corresponding to sixteen vortex contactors 400, as depicted in FIG. 4. Thus, a total of thirty-two vortex contactors can be comprised at the first end 214 operating in parallel, and the vessel 100 may contain a total of sixty-four vortex contactors comprised in the plurality of vortex contactors 270, although any suitable number of vortex contactors may be utilized and in any suitable arrangement, such as aligned or offset.

In addition, a first coalescer 460 can be positioned at the first end 214 and a second coalescer 470 can be positioned at the second end 222. The first and second coalescers 460 and 470 can include, independently, a metal mesh, a hydrophobic mesh, a hydrophilic mesh, one or more metal wires, steel wool, one or more vanes, one or more glass fibers, sand, a coalescing media including one or particulates, or a combination thereof. The vessel 100 can also be divided by a partition or wall 268. Generally, the first end 214 can be a mirror image of the second end 222. As a consequence, only the first end 214 will be described in detail structurally. Generally, a first manifold 420 can communicate the first liquid 50 to the plurality of vortex contactors 270. Particularly, the first manifold 420 can include a conduit 422 that may conduct the first liquid 50 to the plurality of vortex contactors 270. The second liquid, which in this instance can be an intermediate second liquid 160 hereinafter described, can be split into streams 160 provided to the second manifold 440 including a plurality 444 of conduits, namely a first conduit 446 and a second conduit 448. Generally, the first conduit 446 and the second conduit 448 can sandwich the conduit 422. Particularly, the first conduit 446 and the second conduit 448 can share a respective common wall 456, respectively with the first manifold 420.

Referring to FIG. 5, the plurality of vortex contactors 270 can include a first vortex contactor 280 and a second vortex contactor 400. Generally, the vortex contactors 280 and 400 can be substantially mirror images of one another. As a consequence, only the vortex contactor 280 will be discussed in detail. Typically, the first vortex contactor 280 and the second vortex contactor 400 can share a partition 322 that separates the vortex contactors 280 and 400. The vortex contactor 280 can enclose an interior region or vortex zone 298 and include at least one wall or member 290 that forms a swirler 290, as hereinafter described. Moreover, the vortex contactor 280 can be formed about a center 296 and have a perimeter or inner surface 294. Downstream of the swirler 290, a frustum 318, preferably funnical, can be proximate to the swirler 290 and be formed integrally with at least one wall 292. Generally, the first and second liquids 50 and 160 can enter the swirler 290 at the termination of the wall 456, and issue as contacted liquids 328 having two immiscible phases.

Figure 6:
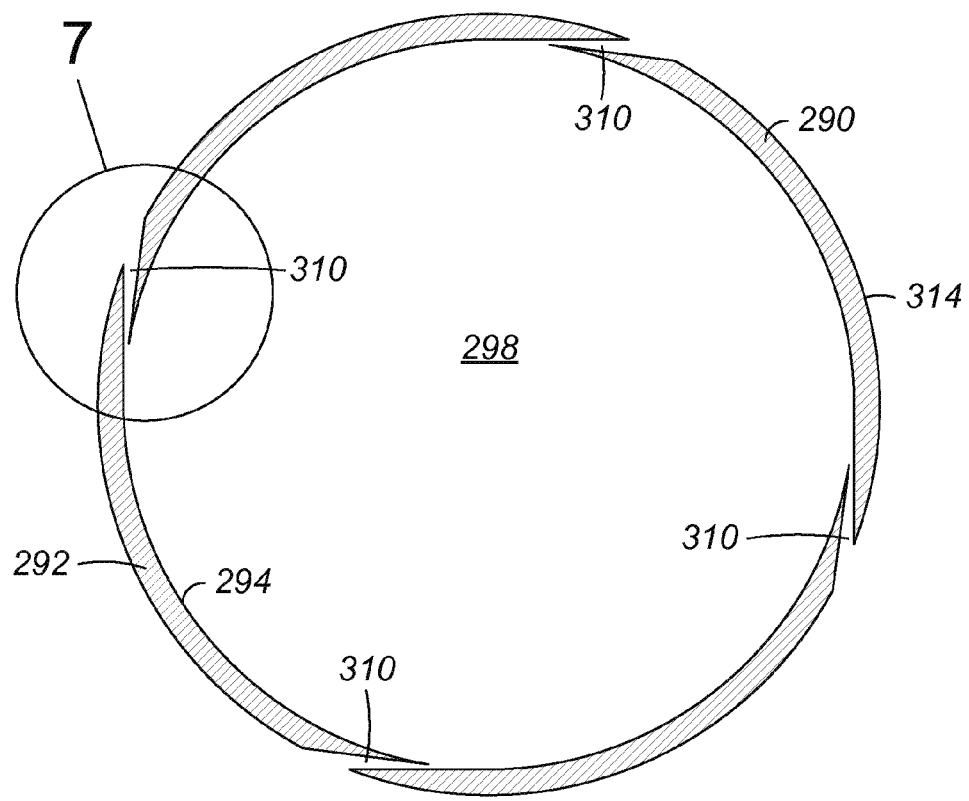
FIG. 6 is a cross-sectional view of a slice of an exemplary swirler.
Figure 7:
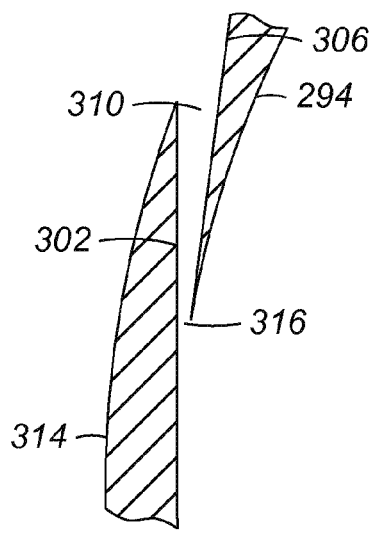
FIG. 7 is an enlarged view of the slice of the exemplary swirler of FIG. 6.
Figure 12:
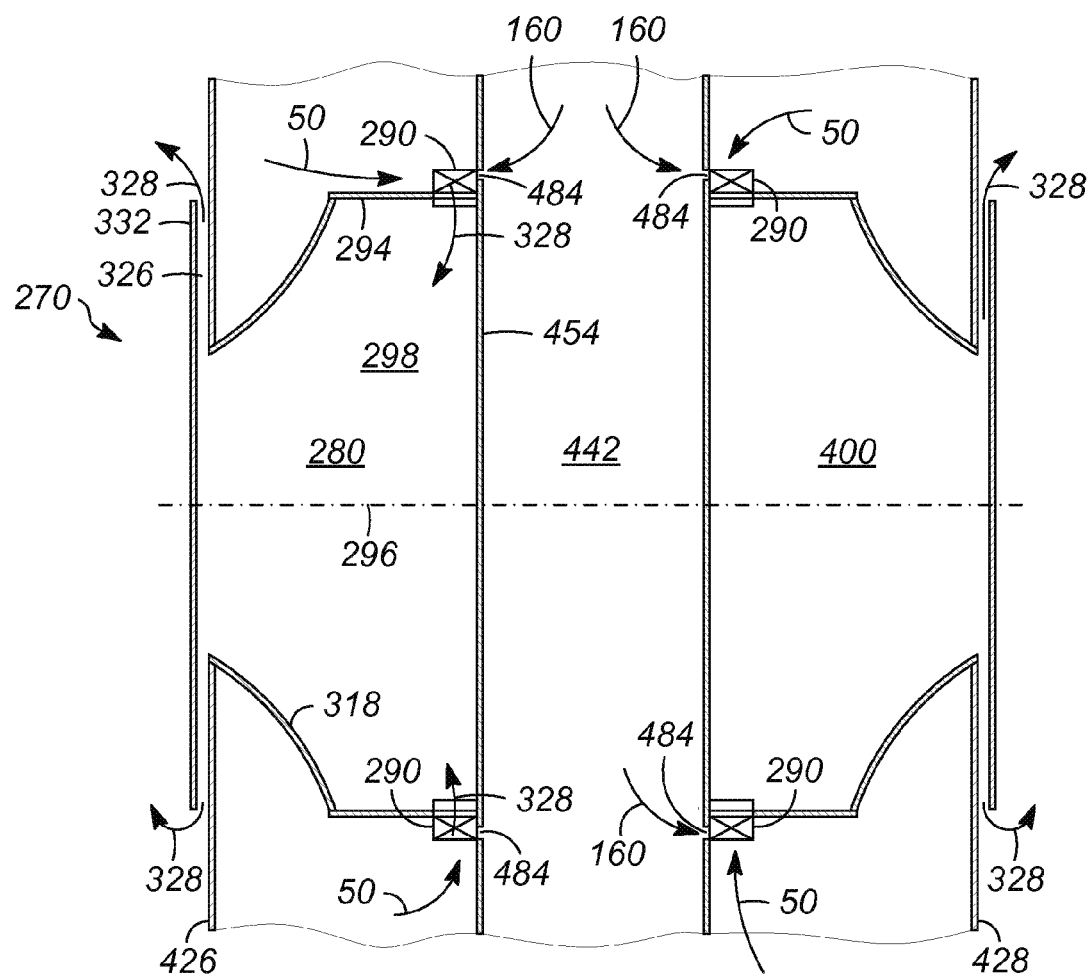
FIG. 12 is a side, elevational, and enlarged view of a portion of the another exemplary vessel depicted in FIG. 10.

Referring to FIGS. 5-7, the swirler 290 can be substantially ring-shaped, and formed as a separate component or formed by at least one wall 292. The member 290 can be positioned within or about the interior region 298 and reside upstream of the frustum 318. Generally, the swirler 290 can form one or more passageways 310 along an exterior or periphery 314 to permit the liquids 50 and 160 to enter. In this exemplary embodiment, four exemplary passageways 310 are depicted, but any suitable number of passageways 310 may be formed in the swirler 290. Generally, each passageway 310 communicating with a respective opening 458 to permit entry of the intermediate second liquid 160.

Often, the swirler 290 can impart a rotational motion to the liquids 50 and 160 passing from an exterior 314 to an inner surface 294. Usually, the each passageway 310 can taper from the exterior 314 to the inner surface 294. Each passageway 310 can be defined by a first side 302 spaced apart from a second side 306 that may taper each passageway 310 to form a slot 316.

Alternatively, the first side 302 can form vanes at an angle of about 90-about 180° with respect to one another that can further taper the passageway 310. As an aside, each side 302 and 306 can, independently, be considered a vane. The tapering of the passageway 310 can facilitate accelerating and imparting a circular motion to the liquids 50 and 160. The sides 302 and 306 can be formed integrally with the swirler 290, or formed as separate components and coupled together to at least partially comprise the swirler 290. The swirler can communicate at low pressure the contacted liquids 328 to the vortex zone 298 at an angular acceleration of no more than about 10 g, or no more than about 8 g in the vortex zone 298. However, the angular acceleration can vary and in other exemplary embodiments be higher at other locations, such as about 70 g exiting from or in the passageway 310 of the swirler 290.

Initially, the contacted liquids 328 can be introduced tangentially and biased toward a perimeter 294 of the interior region 298. Both phases can intimately mix and separate under low g-forces to allow extraction of one or more components, such as one or more sulfur compounds, from the first liquid into the second liquid.

Although not wanting to be bound by theory, the rotational movement of the mixed liquids can accelerate by means of a curved internal structure that may enable the heavier phase to move rapidly toward the vortex contactor walls. Moreover, the frustum can maintain the stability of the vortex and smoothing of pressure and flow. The curved internal structure may include the funnical frustum 318 that may abut the internal wall and taper the inner radius of the liquid-liquid vortex contactor body.

Referring back to FIGS. 1-5, the funnical frustum 318 can be positioned proximate and downstream to the swirler 290 and abut the at least one wall 292. It should be understood that the at least one wall 292 and the funnical frustum 318 can be formed as separate pieces and coupled together, or formed integrally together. The frustum 318 can form a curvature for facilitating the formation of a vortex by the liquids entering the interior region 298 and for collecting the liquids. At least a portion of its curvature can resemble a parabola. Although a parabolic profile is depicted other suitable profiles can include a rectangular, a conical, or a concave profile. Generally, the cross-section of the funnical frustum 318 can resemble any suitable bell curve.

Hence, two phases can be formed into a vortex layer, i.e., a rotating cylindrical body, with the first liquid 50 being the continuous phase and the intermediate second liquid 160 being the disperse phase. The rotational motion of the combined phases can be accelerated by the frustum 318, preferably funnical. The droplets of the intermediate second liquid 160 can coalesce at least partially stratifying the intermediate second liquid 160 from the first liquid 50 to begin separation.

The contacted liquid 328 can travel within interior region 298 and pass to an outlet end 332 of a channel 326 and exit. The first liquid 50 can generally be at least partially extracted of one or more sulfur compounds and exit the vortex contactor 280. Often, the contacted liquid 328 begins to separate into different phases after exiting the vortex contactor 280 with the second liquid 160 falling in the direction of gravity to the bottom 254 having been at least partially saturated by one or more sulfur compounds.

The plurality of vortex contactors 270 can provide the first and second liquids 50 and 160 upstream of the first coalescer 460. The vortex contactor 400 can provide the liquids directly to the first coalescer 460 where the first liquid 50 can pass through the first coalescer 460 while the intermediate second liquid 160 can drop to the bottom 254 of the vessel 100. The vortex contactor 280 can provide the first and second liquids 50 and 160 towards the first end 214 where the liquids 50 and 160 can migrate through the ducts 266 and proceed toward the first coalescer 460. Again, these liquids 50 and 160 can separate with the lighter first liquid 50 rising and the heavier second liquid falling, thus some separation can occur before reaching the first coalescer 460. Generally, separation of fine droplets of the intermediate second liquid 160 in the first liquid 50 occurs after passage through the first coalescer 460.

In operation, a first liquid 50 can be provided to the first inlet 232. The first liquid 50 can be passed through the plurality of vortex contactors 270 by being contacted with the intermediate second liquid 160 provided by the split streams 160. The first and second liquids 50 and 160 can be contacted with the plurality of vortex contactors 270 for extracting one or more sulfur compounds with the first liquid 50 rising and the intermediate second liquid 160 falling. Generally, the intermediate second liquid 160 can be dispersed within the first liquid 50 and droplets can coalesce. The first liquid 50 being contacted with the intermediate second liquid 160 can have one or more thiol compounds removed from the first liquid 50 by being extracted into the intermediate second liquid 160. At this point, the first liquid 50 can be at least partially extracted and the intermediate second liquid 160 can be at least partially saturated, or fully saturated or spent. The first and second liquids 50 and 160 can pass through the first coalescer 460 to further coalesce fine droplets of the intermediate second liquid 160. The intermediate second liquid 160 can exit the second outlet 450 as a spent second liquid 180.

The first liquid 50 can pass through the intermediate first liquid outlet 248 as an intermediate first liquid 120. Thus, the intermediate first liquid 120 can exit the top 246 from the intermediate first liquid outlet 248 at "B" and re-enter the first side 230 at the intermediate first liquid inlet 234. Also being provided can be a second liquid 60 through second inlets 242. Generally, the second liquid 60 is a fresh alkaline stream, such as an aqueous solution of sodium or potassium hydroxide, or ammonia. Thus, the intermediate first and second liquids 120 and 60 can be contacted counter-currently at the second end 222. After passing the intermediate first and second liquids 120 and 60 through the plurality of vortex contactors 270, similarly as described above, the intermediate first and second liquids 120 and 60 can either pass directly through the second coalescer 470 or pass through a duct 266 and then through the second coalescer 470, similarly as described above for the first coalescer 460. The intermediate first liquid 120 can rise and the second liquid 60 can fall. After contacting, the intermediate first liquid 120 can have almost all of the one or more sulfur compounds extracted while the second liquid 60 can be at least partially saturated.

The contacted liquid 328 can separate by coalescing into droplets of the second liquid 60 from the intermediate first liquid 120 with the intermediate first liquid 120 rising and the second liquid 60 falling. Further separation of fine droplets can occur when the liquids 60 and 120 pass through the second coalescer 470. The hydrocarbon can exit the first outlet 430 as a first liquid product 140 and the second liquid 60 may exit the second outlet 450 as the intermediate second liquid 160. Usually, the intermediate second liquid 160 exits the bottom 254, is split into the streams 160, and enters respective first and second conduits 446 and 448 described above.

The first liquid product 140 can include no more than about 1 ppm, by weight, of, independently, a cation, such as sodium or potassium, representative of the alkaline liquid, and one or more sulfur compounds. Alternatively, the hydrocarbon product may have, independently, about 1-about 10 ppm, by weight, of the cation and one or more sulfur compounds. Although not wanting to be bound by theory, it is generally contemplated that two or more stages of contacting can result in a first liquid product having no more than about 1 ppm, by weight, of, independently, cation and one or more sulfur compounds.

Referring to FIGS. 8-12, another version of the vessel 100 is depicted. As used herein, components having substantially similar functionality but albeit different shapes may be indicated with the same numeral as the previous version depicted in FIGS. 1-7.

The vessel 100 can include the plurality of vortex contactors 270, the first coalescer 460, and the second coalescer 470. The vessel 100 may also have a partition or wall 268. In this exemplary embodiment, the first manifold 420 can include a plurality of conduits, namely a first conduit 426 and a second conduit 428 that sandwich a conduit 442 of the second manifold 440. In this exemplary embodiment, the first liquid 50 can be provided through a plurality of conduits 424 that can sandwich the conduit 442 providing the intermediate second liquid 160 via the second manifold 440. Referring to FIG. 10, the conduit 442 can be positioned between the first vortex contactor 280 and the second vortex contactor 400. Particularly, the conduit 442 can include a wall 454 surrounding the void within the conduit that can serve as a portion of the vortex contactor 280 and the second vortex contactor 400. Generally, each passageway 310 communicating with a respective opening 484 to permit entry of the intermediate second liquid 160.

The first liquid 50 can be provided by the conduits 426 and 428 that may at least partially share a wall with the conduit 442. Typically, the intermediate second liquid 160 from the conduit 442 can be provided to the swirler 290 for each vortex contactor 280 and 400. The first liquid 50 and the intermediate second liquid 160 can enter the swirler 290 and contact to facilitate the extraction of one or more thiol compounds from the first liquid 50 into the intermediate second liquid 160. The contacted liquids 328 may exit the swirler 290.

As described above, the contacted liquid 328 can exit the channel 326. The first and intermediate second liquids 50 and 160 can proceed through the vessel 100 similarly as described above, particularly passing through the coalescers 460 and 470 and eventually exiting the first outlet 430 and the second outlet 450. Moreover, the vessel 100 can receive a second liquid 60 in a second inlet 438, and proceed through the vessel 100 to become the intermediate second liquid 160.

Figure 13:
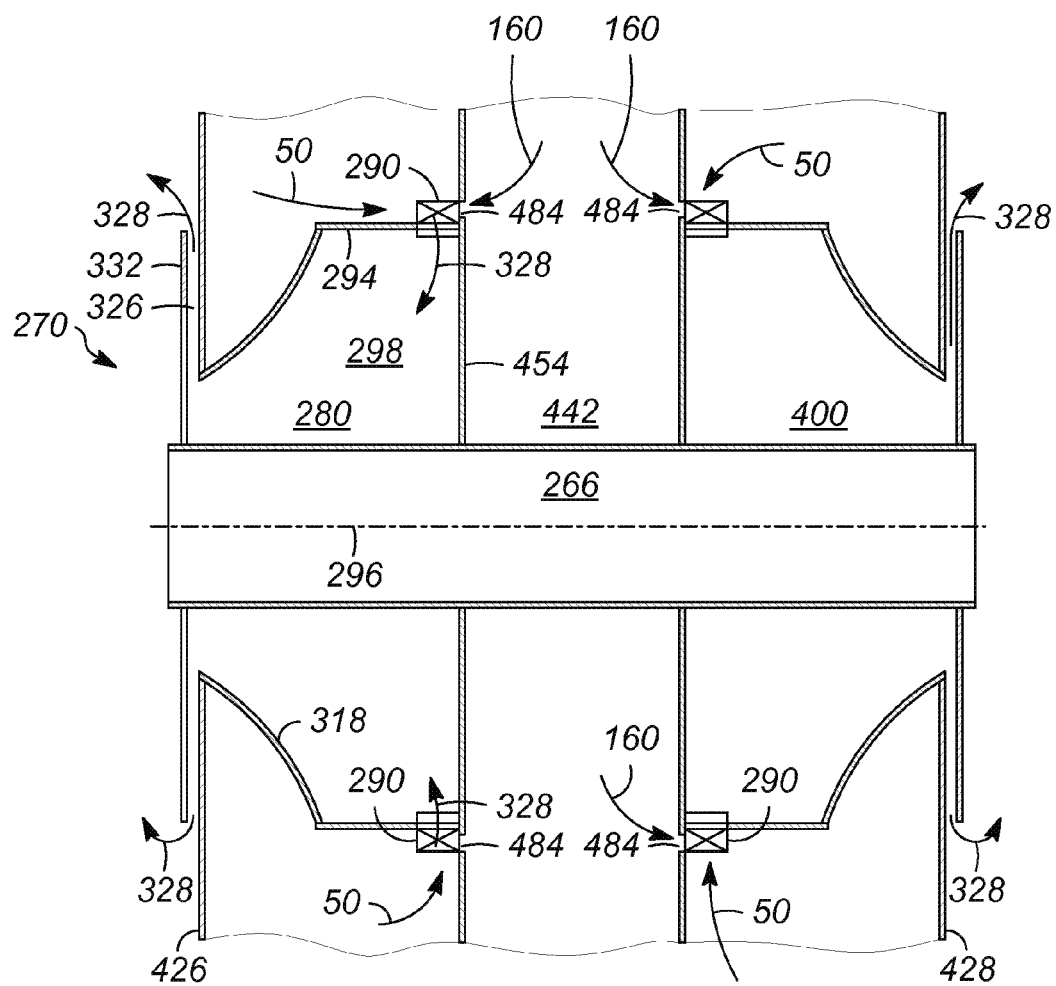
FIG. 13 is a side, elevational, and enlarged view of a portion of a further exemplary vessel.

Referring to FIG. 13, another version of the plurality of vortex contactors 270. In this exemplary embodiment, a respective duct 266 can form about a center 296 line and pass through the vortex contactor 280, the vortex contactor 400, and the conduit 442. Having the one or more ducts 266 passing through respective vortex contactors 280 and 400 can allow the vessel 100 to contain more vortex contactors by not having separate ducts 266.

Figure 14:
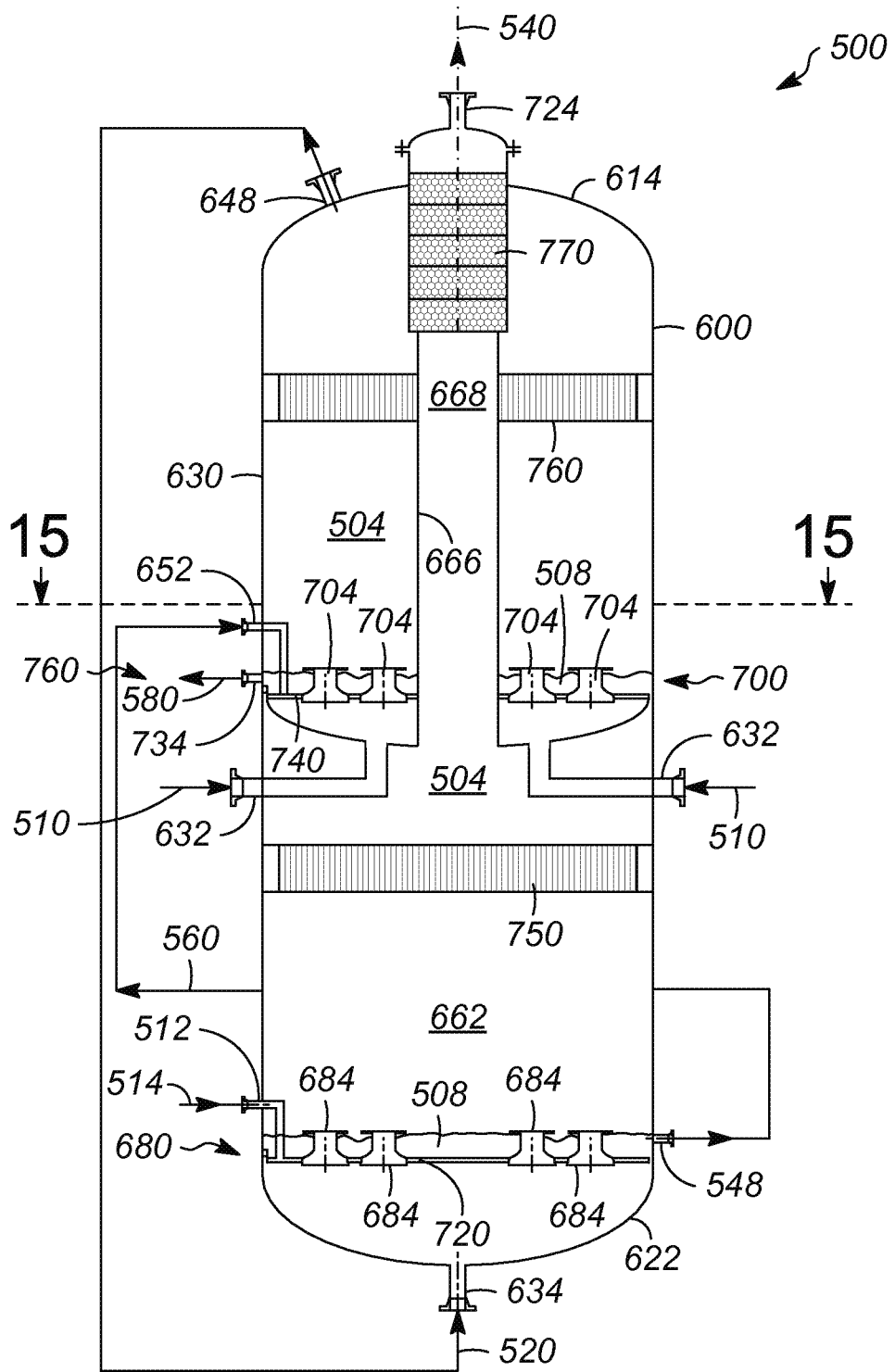
FIG. 14 is an elevational and cross-sectional view of yet another exemplary embodiment.
Figure 15:
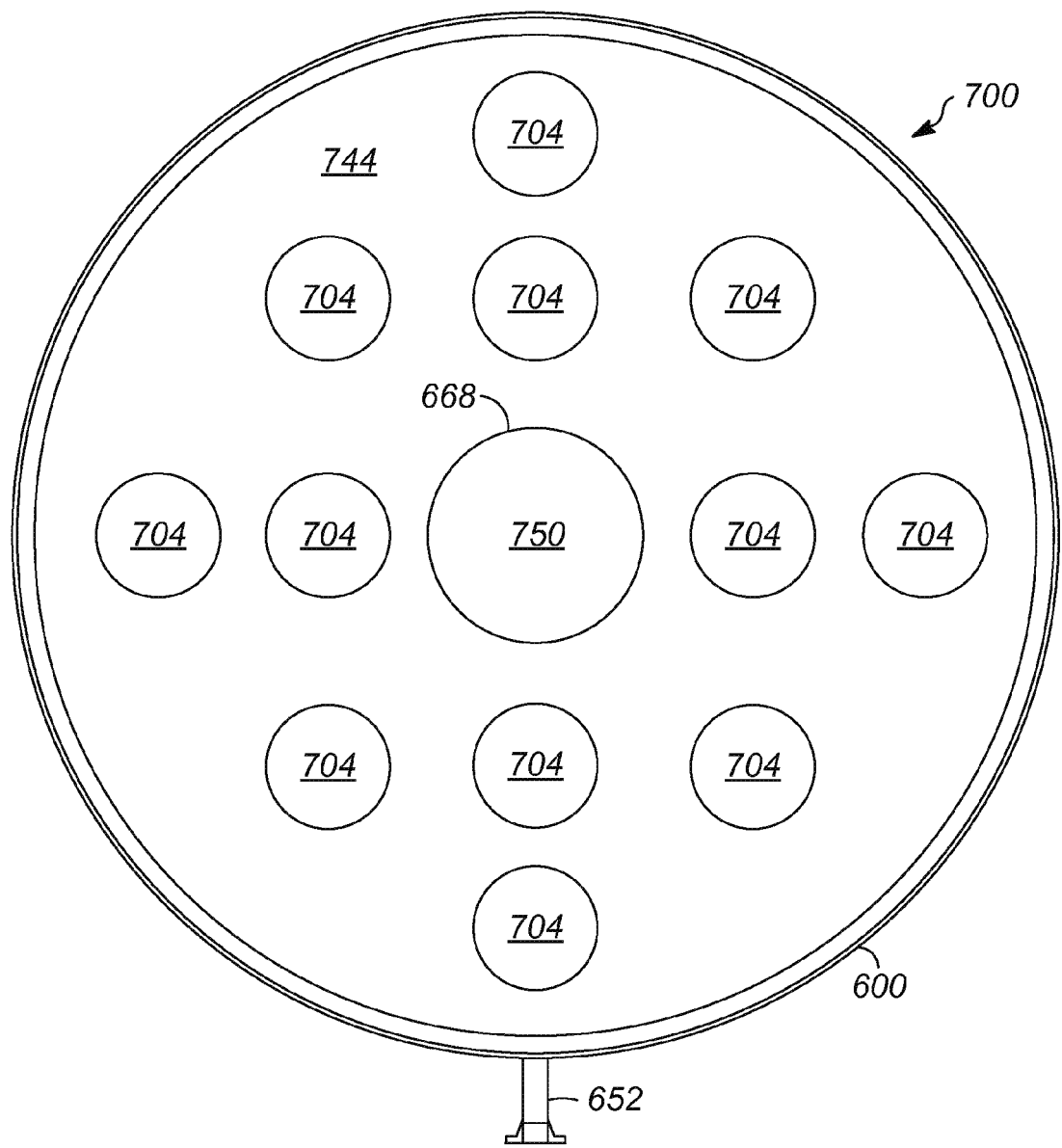
FIG. 15 is a cross-sectional view of the yet another exemplary vessel along lines 12-12 of FIG. 14.
Figure 16:
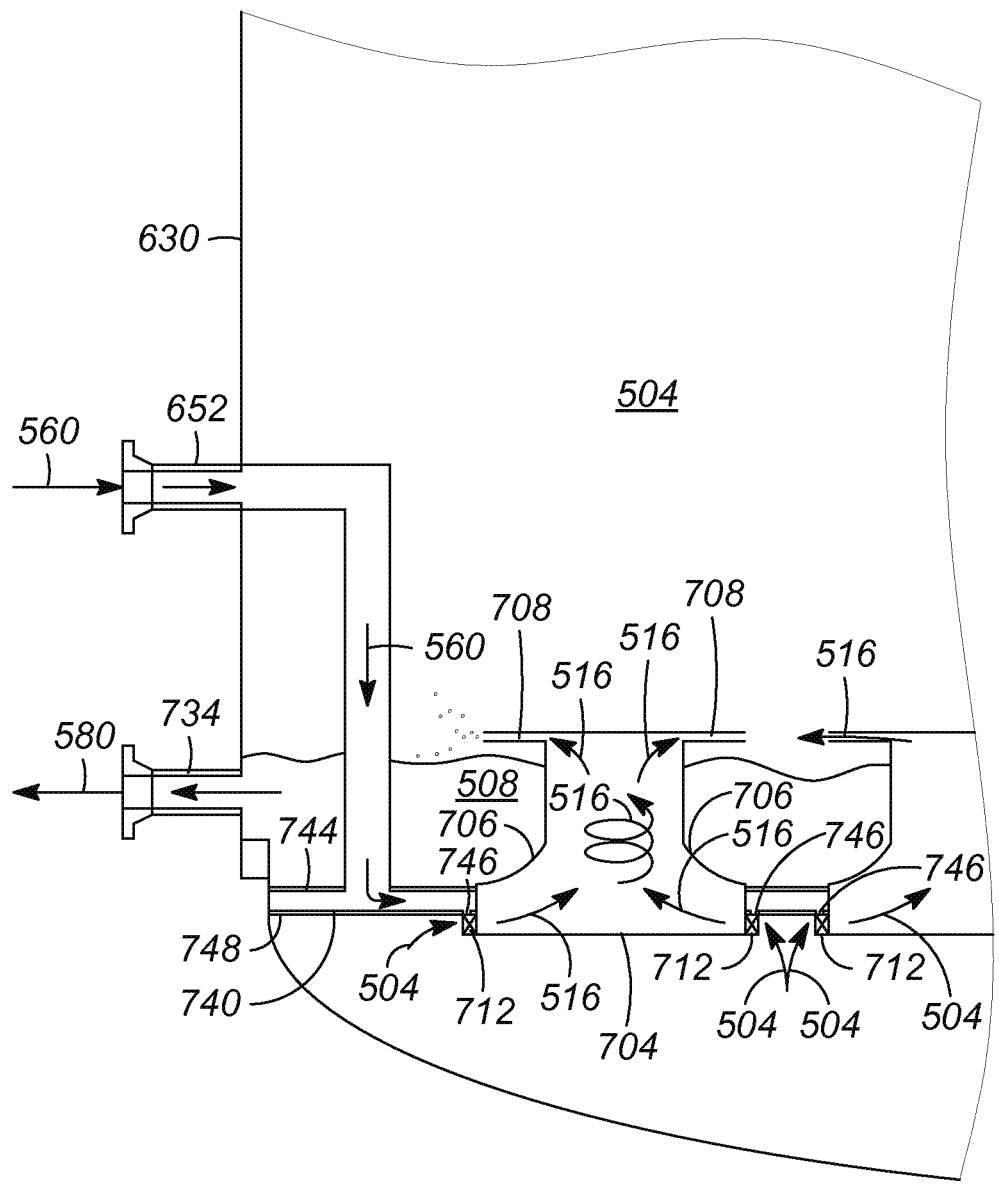
FIG. 16 is an enlarged, cross-sectional view of a portion of the yet another exemplary vessel.

Referring to FIGS. 14-16, another vessel 500 for removing one or more sulfur compounds can include a substantially cylindrical shell 600 orientated substantially vertical with the vertical height being greater than the horizontal length. In this exemplary embodiment, the substantially cylindrical shell 600 can surround an interior space 662 and have a top end 614 and a bottom end 622. Generally, a substantially cylindrical wall 630 can be coupled to the ends 614 and 622 forming hemi-spheres or domes. The vessel 500 can include first inlets 632 on opposing sides of the shell 600, a second liquid inlet 512, an intermediate first liquid inlet 634, an intermediate first liquid outlet 648, an intermediate second liquid inlet 652, an intermediate second liquid outlet 548, a first liquid outlet 724 and a second liquid outlet 734. Generally, the substantially cylindrical shell 600 can house an internal compartment 666 for allowing a two stage countercurrent extraction of one or more sulfur compounds from a first liquid 510 into a second liquid 514.

At the bottom end 622, the substantially cylindrical shell 600 can house a first group of vortex contactors 680, and a first coalescer 750. Generally, the first coalescer 750 can include a metal mesh, a hydrophobic mesh, a hydrophilic mesh, one or more metal wires, steel wool, one or more vanes, one or more glass fibers, sand, a coalescing media including one or particulates, or any combination thereof.

At the top end 614, the internal compartment 666 can house a second group of vortex contactors 700, as illustrated by four vortex contactors 704 as depicted in FIG. 11. In addition, the internal compartment 666 can house an annulus-shaped second coalescer 760 and form a channel 668 that in turn can receive a third coalescer 770. The second coalescer 760 and the third coalescer 770 can include, independently, the same components as described above for the first coalescer 750. The plurality of first group and second group of vortex contactors 680 and 700 can be radially arranged about a channel 668.

Although only four vortex contactors 704 are shown in the second group of vortex contactors 700 in FIG. 14, it should be understood that the vortex contactors 704 can be arranged to provide any suitable number of vortex contactors, such as the twelve vortex contactors, as depicted in FIG. 15. Also, the vortex contactors can be arranged in any suitable manner, such as aligned or offset. In addition, the first group of vortex contactors 680 can be similarly radially arranged including a host of vortex contactors at a lower elevation. Vortex contactors 704 and 684 can operate similarly, and as described above for the vessel 100.

In operation, the first liquid 510 can be provided to the first inlets 632 and rise within the internal compartment 666 of the first stage. The first liquid 510 is provided about halfway up the vessel 500. An intermediate second liquid 560 as hereinafter described can be provided to an intermediate second liquid inlet 652 and a manifold 740, which may include a top plate 744 and a bottom plate 748, as depicted in FIG. 16. The intermediate second liquid 560 can travel between the plates 744 and 748 to the vortex contactors 704. Each vortex contactor 704 of the plurality of vortex contactors 700 as well as the vortex contactors 684 are substantially the same. As a consequence, only the vortex contactor 704 will be described in further detail.

Referring to FIGS. 14-16, the first liquid 504 rises and enters the swirler 712, which can be substantially similar to the swirler 290 described above, along with the intermediate second liquid 560, which can pass through an opening 746 in the bottom plate 748. The contacted liquids 516 can continue to rise within a space defined by a frustum 706, which may be inverted in this exemplary embodiment and otherwise be substantially similar to frustum 318 described above. The contacted liquids 516 can continue to rise toward the passageway 708. The contacted liquids 516 can exit the passageway 708 and begin to coalesce. The contacted liquids 516 can coalesce into a hydrocarbon phase 504 and an alkaline phase 508. The alkaline phase 508 passes through the second liquid outlet 734 and can exit the vessel 500 as a spent second liquid 580. The hydrocarbon phase 504 can rise and pass through the second coalescer 760, which can be shaped like an annulus corresponding to the shape of the internal compartment 666, and exit the first liquid intermediate outlet 648. The intermediate first liquid 520 can be routed outside the vessel 500 and returned to the intermediate first liquid inlet 634 of the second stage. The intermediate first liquid 520 can rise within the vessel 500 and again be contacted with a second liquid 514 provided to the second liquid inlet 512 through another manifold 720, similarly as described above for the vortex contactor 704. The second liquid 514 in this instance can be a fresh alkaline solution. Again, the liquids 514 and 520 can be contacted in a vortex contactor 684 and separated into two phases, namely a hydrocarbon phase 504 and an alkaline phase 508. The alkaline phase 508 can be passed through the second liquid intermediate outlet 548 as the intermediate second liquid 560 and routed to the intermediate second liquid inlet 652, as described above. The hydrocarbon phase 504 can rise past the second coalescer 760 and into the channel 668 formed by the internal compartment 666. The hydrocarbon phase 504 can rise past the second coalescer 760 into the channel 668 and past the third coalescer 770. Any second liquid 514 entrained within the intermediate first liquid 520 can form droplets and coalesce and drop to the alkaline phase 508 proximate to the vortex contactor 684. The hydrocarbon phase 504 can continue to rise and exit the vessel 500 via the first outlet 724 as a first liquid product 540. During the contacting of the first and second liquids, any sulfur compounds can be extracted from the first liquid 510 into the second liquid 514. The first liquid product can have the same quantities of cation and one or more sulfur compounds, as described above for the first liquid product 140. Although one or two stages are disclosed, it should be understood that more than two stages may be utilized.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for removing one or more sulfur compounds from a first liquid comprising:
    A) passing the first liquid through a first inlet and a second liquid through a second inlet of a vessel, wherein the vessel further comprises:
        1) a plurality of vortex contactors, wherein the plurality of vortex contactors comprises at least a first and a second vortex contactor, each vortex contactor in turn comprising:
            a) at least one wall forming a perimeter about an interior region and comprising a first side and a second side forming a passageway communicating liquid from an exterior to the interior region; and
            b) a frustum positioned proximate to the passageway and abutting the at least one wall; and
        2) a first outlet and a second outlet;
    B) swirling the first and second liquids at no more than bout 10 g,
    C) passing the first and second liquids through the passageway of the first vortex contactor and passing the first and second liquids though the passageway of the second vortex contactor for facilitating contacting of the first and second liquids to extract the one or more sulfur compounds from the first liquid to the second liquid; and
    D) passing the first liquid through the first outlet and the second liquid through the second outlet.

2. The process according to claim 1, wherein the swirling of the first and second liquids is at no more than about 8 g.

3. The process according to claim 1, wherein the vessel is substantially cylindrical and orientated substantially horizontal, and the vessel further comprises a first end, a second end, a first side, a second side, a top, and a bottom, wherein the first inlet is formed in the first side and the second inlet is formed in the second side.

4. The process according to claim 1, wherein the frustum comprises a funnical frustum to direct liquids to a center of the respective vortex contactor.

5. The process according to claim 1, wherein the first vortex contactor abuts the second contactor.

6. The process according to claim 5, further comprising passing the first liquid from the first inlet to a first manifold and the second liquid from the second inlet to a second manifold wherein the first manifold comprises a conduit and the second manifold comprises a plurality of conduits wherein the conduits of the second manifold sandwich the conduit of the first manifold; and passing the first liquid from the first manifold to the plurality of vortex contactors, and passing the second liquid from the second manifold to the plurality of vortex contactors.

7. The process according to claim 6, wherein the plurality of conduits of the second manifold comprises at least a first conduit and a second conduit wherein the first conduit communicates with the first vortex contactor and the second conduit communicates with the second vortex contactor.

8. The process according to claim 5, further comprising passing the first liquid from the first inlet to a first manifold and the second liquid from the second inlet to a second manifold wherein the first manifold comprises a plurality of conduits and the second manifold comprises a conduit wherein the conduits of the first manifold sandwich the conduit of the second manifold; and passing the first liquid from the first manifold to the plurality of vortex contactors, and passing the second liquid from the second manifold to the plurality of vortex contactors.

9. The process according to claim 1, wherein the vessel is substantially cylindrical and orientated substantially vertical, and the vessel further comprises a first end, a second end, a first side, a second side, a top, and a bottom, wherein the first inlet is formed in the first side and the second inlet is formed on the second side.

10. The process according to claim 9, wherein plurality of vortex contactors comprises a first group of vortex contactors at a first elevation and a second group of vortex contactors at a second elevation.

11. The process according to claim 1, wherein the first and second liquids are contacted counter-currently in the passageways of the vortex contactors.

* * * * *